(12) United States Patent
Miller et al.

(10) Patent No.: US 6,200,011 B1
(45) Date of Patent: Mar. 13, 2001

(54) FIXED-HOUSING AIMABLE-BEAM SPOTLIGHT LUMINAIRE

(76) Inventors: Jack V. Miller; Ruth Ellen Miller, both of R.R. 4 Box 746, Seaford, Sussex County, DE (US) 19973

( * ) Notice: Subject to any disclaimer, the term of this patent is extended or adjusted under 35 U.S.C. 154(b) by 0 days.

(21) Appl. No.: 09/347,739

(22) Filed: Jul. 6, 1999

Related U.S. Application Data

(63) Continuation-in-part of application No. 08/911,624, filed on Aug. 15, 1997, now Pat. No. 5,907,648.

(51) Int. Cl.[7] .................. F21V 8/00; G02B 6/32

(52) U.S. Cl. .............. 362/554; 362/556; 362/560; 385/31; 385/32; 385/33; 385/901

(58) Field of Search .................. 385/33, 35, 31, 385/32, 115, 116, 119, 120, 147, 901; 362/554, 556, 560, 141, 147, 227, 449, 551, 559

(56) References Cited

U.S. PATENT DOCUMENTS

| | | | |
|---|---|---|---|
| 5,303,125 | * | 4/1994 | Miller ................................ 362/554 |
| 5,907,648 | * | 5/1999 | Miller et al. ......................... 385/33 |

* cited by examiner

Primary Examiner—Phan T. H. Palmer

(57) ABSTRACT

An aimable luminaire has a lamp emitting light at the focus of a beam-forming lens held in a tubular housing having a lens on a central optical axis. The lamp is held in a lamp retainer which is transversely adjustable off the central axis of the housing and lens and axially adjustable with respect to the lens. When the lamp is moved off the optical axis, an off-axis beam is projected, and when the lamp is moved axially moved with respect to the lens the beam angle is zoomed larger or smaller. Rotation of housing in azimuth can then aim the light beam anywhere within a cone inscribed by rotation of the off-axis beam angle, thus providing adjustment in both elevation and azimuth. In a preferred embodiment either the transverse or axial position of the lamp may be the lamp may be adjusted from the proximal direction, above the ceiling, or from the distal direction by removing the lens from the distal end.

7 Claims, 5 Drawing Sheets

FIXED-HOUSING AIMABLE-BEAM SPOTLIGHT LUMINAIRE

This application is a continuation in part of Ser. No. 08/911,624 filed Aug. 15, 1997, now issued as U.S. Pat. No. 5,907,648.

BACKGROUND

Field of the Invention

This invention applies to the field of lighting spotlights capable of being mounted to a rigid planar surface, such as a ceiling or wall, and being aimable to direct a light beam at an object; and more particularly spotlights capable of also zooming the light beam.

BACKGROUND

Description of Prior Art

Presently known aimable spotlights normally use a collimating lens with a light source, such as an incandescent filament or small arc tube, at the focus of the lens. The emitted beam is normally on an optical axis from the center of the light source through the optical center of the lens.

Aiming the beam of presently-known prior-art spotlights is usually accomplished by aiming the housing holding the light source and the lens. There are many prior-art methods for aiming a such light beams. The first method is by pivotally mounting the housing on the horizontal axis of a yoke, and then rotating the yoke about a vertical axis, forming an azimuth-elevation, or "AZ-EL" mount, such as is shown in FIG. 1 of the Applicant's U.S. Pat. No. 4,822,292 for track lighting. A second method for aiming a spotlight is by attaching it to a movable or flexible arm, known as a "goose-neck" mount, such as is shown in the Applicant's U.S. Pat. No. 3,652,848. All of the above methods require the entire luminaire to be within the room in which they are mounted. A third method for aiming a spotlight is to employ a semi-recessed housing in a spherical mounting, commonly called an "eyeball"fixture; a very old configuration used for airline passenger reading lights. This approach can substantially recess the housing, but it makes the luminaire about three times the diameter of the actual lens. A third method for aiming a light beam is to rigidly mount the housing and provide an azimuth-elevation aiming mirror on a bracket mounting, such as is shown in Applicant's U.S. Pat. No. 5,303,125. This is an aesthetic improvement that mounts the housing above the ceiling plane, but it still requires an optical element, i.e., the mirror, to hang down from the ceiling. The primary disadvantages in all the prior-art methods for aiming light fixture beams is that they are generally complex, and most extend into the room, below the ceiling.

OBJECTS AND ADVANTAGES

The primary object of the present invention is to provide a compact, aimable spotlight luminaire that may be entirely recessed into a ceiling surface, in which the lens is fixed, and wherein the beam may be aimed without moving any part of the luminaire that is below the ceiling surface. Such a general configuration is shown in the applicants' U.S. Pat. No. 5,907,648, entitled Aimable-Beam Fiber Optic Luminaire. The primary advantage of such a luminaire is the clean appearance of having only the lens and a thin, surrounding bezel visible, with no visible arm, gooseneck, trunnion, eyeball socket or even a mirror protruding into the room. Another advantage is simplicity and low cost of manufacture.

DETAILED DESCRIPTION OF THE DRAWINGS

Figure 1:
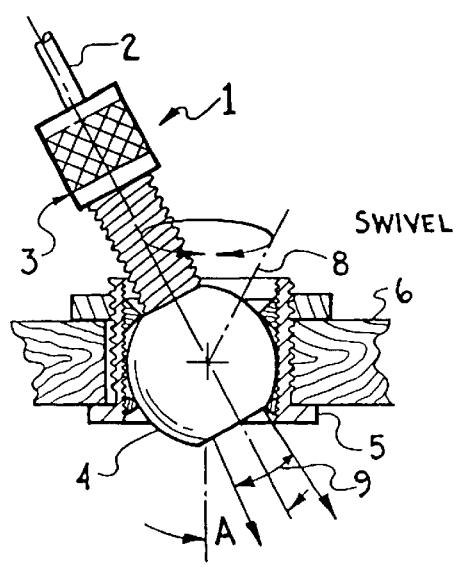
FIG. 1 is a side partial cross-sectional view of a prior art fiber-optic eyeball spotlight luminaire shown mounted in a ceiling.

In FIG. 1 a typical prior-art fiber-optic spotlight luminaire 1 is shown having a light-emitting fiber-optic light guide 2 disposed in a housing 3 having a spherical body 4 adjustably mounted within a mounting 5, mounted in a planar structure 6, shown as a ceiling panel. Housing 3 is free to swivel within a conical arc 8 to position an emitted beam 9 anywhere within an off-axis angle A to aim the light beam.

Figure 2:
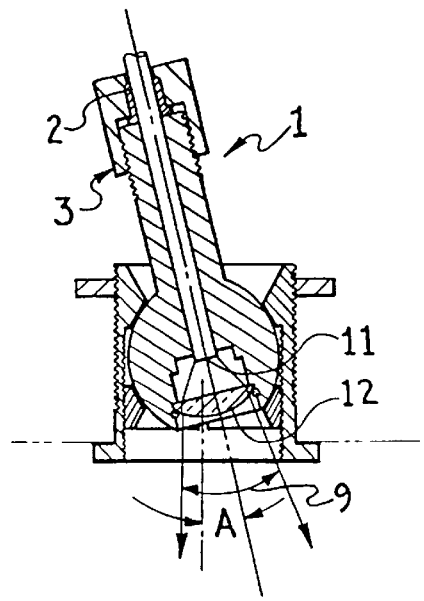
FIG. 2 is a side cross-sectional view of the luminaire of FIG. 1

In FIG. 2 the typical prior art luminaire 1 of FIG. 1 is shown with the light emitting end 11 of light guide 2 positioned to emit light through a lens 12 to produce beam 9, aimable anywhere within off-axis angle A.

Figure 3:
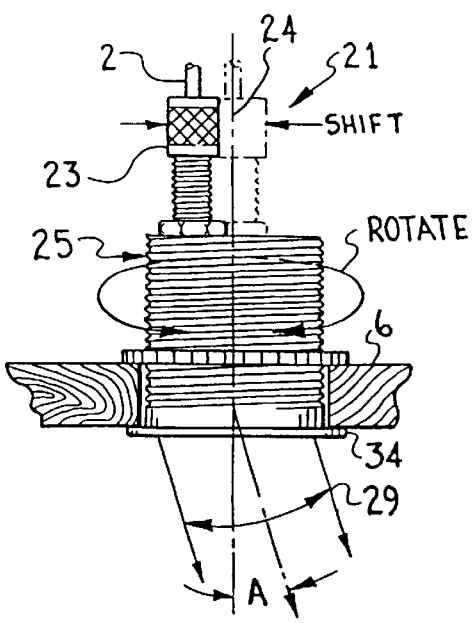
FIG. 3 is a side elevation view of another prior-art aimable fiber-optic spotlight luminaire, shown mounted in a ceiling; the applicants' 5,907,648 patent.

In FIG. 3 the side elevation view of an aimable fiber-optic spotlight luminaire 21 according to the applicants' prior art '648 patent is shown having a light-emitting fiber-optic light guide 2, receiving light from a remote source which is not shown. Light guide 24 is disposed within light-source retainer 23 which is transversely adjustable to shift off a central axis 24 within a housing 25. Housing 25 may be rotated in any azimuth direction, whereby an emitted beam 29 by the transverse adjustment of light-source retainer 23 and the rotation of hosing 25 can aim the light beam 29 anywhere within off-axis angle A.

Figure 4:
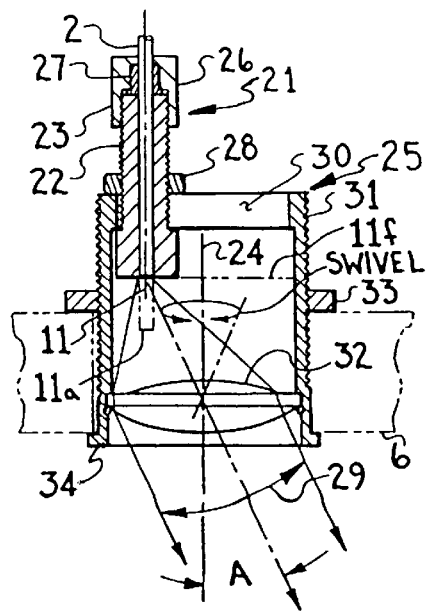
FIG. 4 is a side cross-sectional view of the luminaire of FIG. 3.

In FIG. 4 the side elevation view of FIG. 3 is shown according to the applicants' prior art '648 patent as a cross-sectional view of the aimable fiber-optic spotlight luminaire 21, wherein fiber-optic light guide 2 has its light-emitting end 11 positioned off the optical axis 24 of a lens 23 and in an approximate focal plane 11f of lens 32. Light source retainer 23 includes a tubular retainer 22 which retains fiber 2 with a compression collet 27 tightened by a locking chuck 26. Light source retainer 23 is transversely adjustable by loosening a retaining nut 28, sliding stem 22 transversely in a slot 30 in proximal end 31 of housing 25 to shift fiber 2 off optical axis 24, and re-tightening nut 28; whereby emitted beam 29 may be aimed by the transverse adjustment of light-source retainer 23 and the rotation of housing 25 anywhere within off-axis angle A. This produces the function of swiveling beam 29 in a conical pattern equivalent to that of the eyeball luminaire of FIG. 1, but with housing 25 rotatable in the ceiling 6 by loosening a lock ring 33 which is threadably engaged with housing 25 and applies a holding force on planar structure 6 with flange 34.

Figure 5:
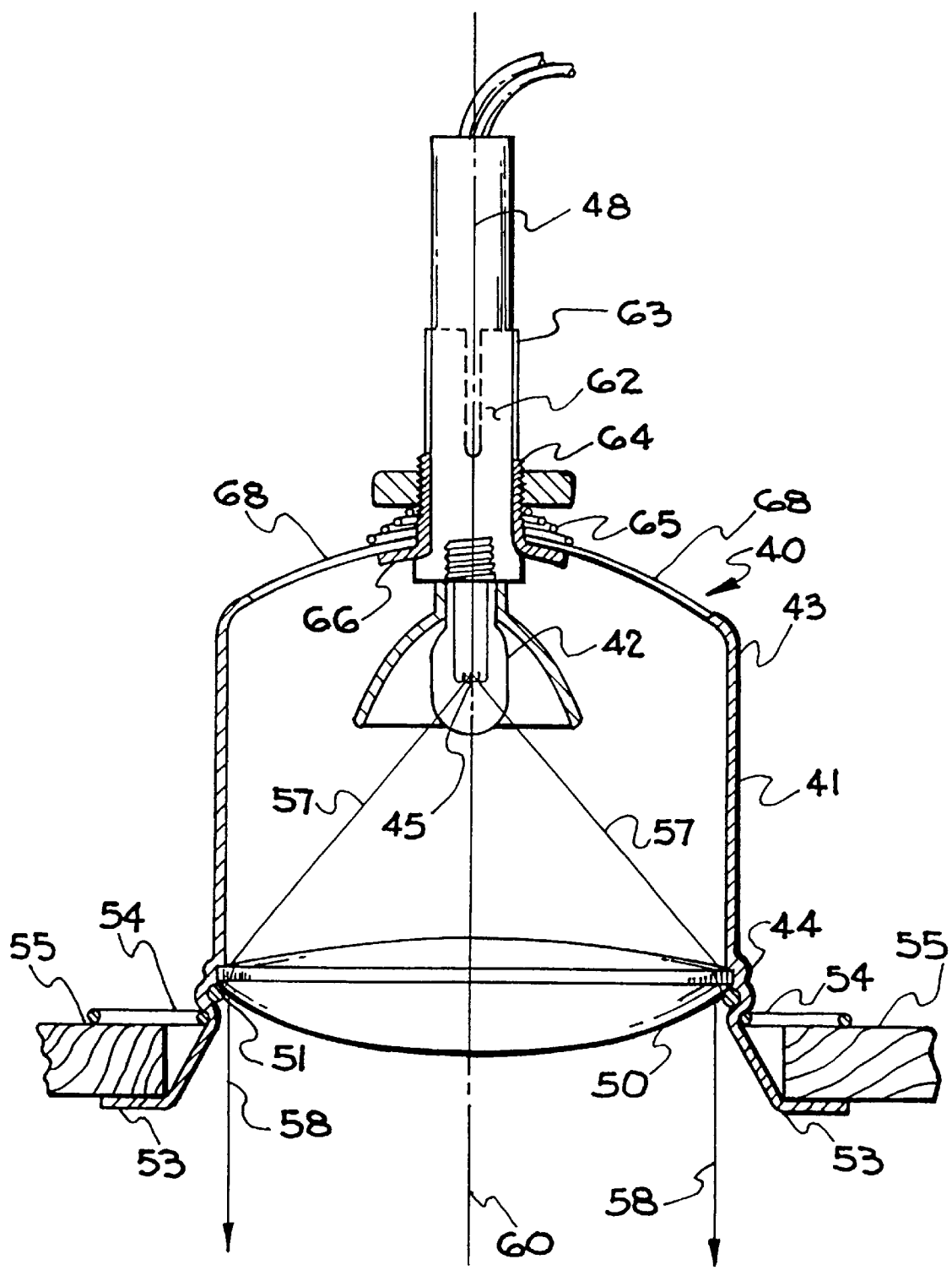
FIG. 5 is a side cross-sectional view of an aimable-beam luminaire according to the present invention, shown producing a narrow spotlight beam on the nadir axis.

In FIG. 5 a side cross-sectional view of an aimable-beam luminaire 40 according to the present invention is shown with the lamp 42 in a generally cylindrical housing 41 having a proximal end 43 and a distal end 44. Lamp 42 is positioned at the focus 45 of a lens 50 and on optical axis 48, also on nadir axis 60. Lens 50 is retained in housing 41 by a resilient retaining ring means 51 at housing distal end 44, said distal end also having a flange 53 and a spring means 54 to hold the luminaire in a typical ceiling panel 55, and to permit azimuth rotation of luminaire 40. Light rays 57 from lamp 42 are generally collimated by lens 50 producing a narrow spotlight beam 58 about nadir axis 60.

Lamp 42 is held in an elongated lampholder 62 which is frictionally engaged into the proximal end 63 of tube 64 to permit axial adjustment of lamp 42 with respect to lens 50. Tube 64 has a distal end 65 including an axial frictional engagement of spring 65 and flange 66 with a slot 68 extending transversely across proximal end 43 of housing 41. Slot 68 is preferably arcuate as shown, but for economy purposes may be a flat slot across proximal end 43 of housing 41.

Figure 6:
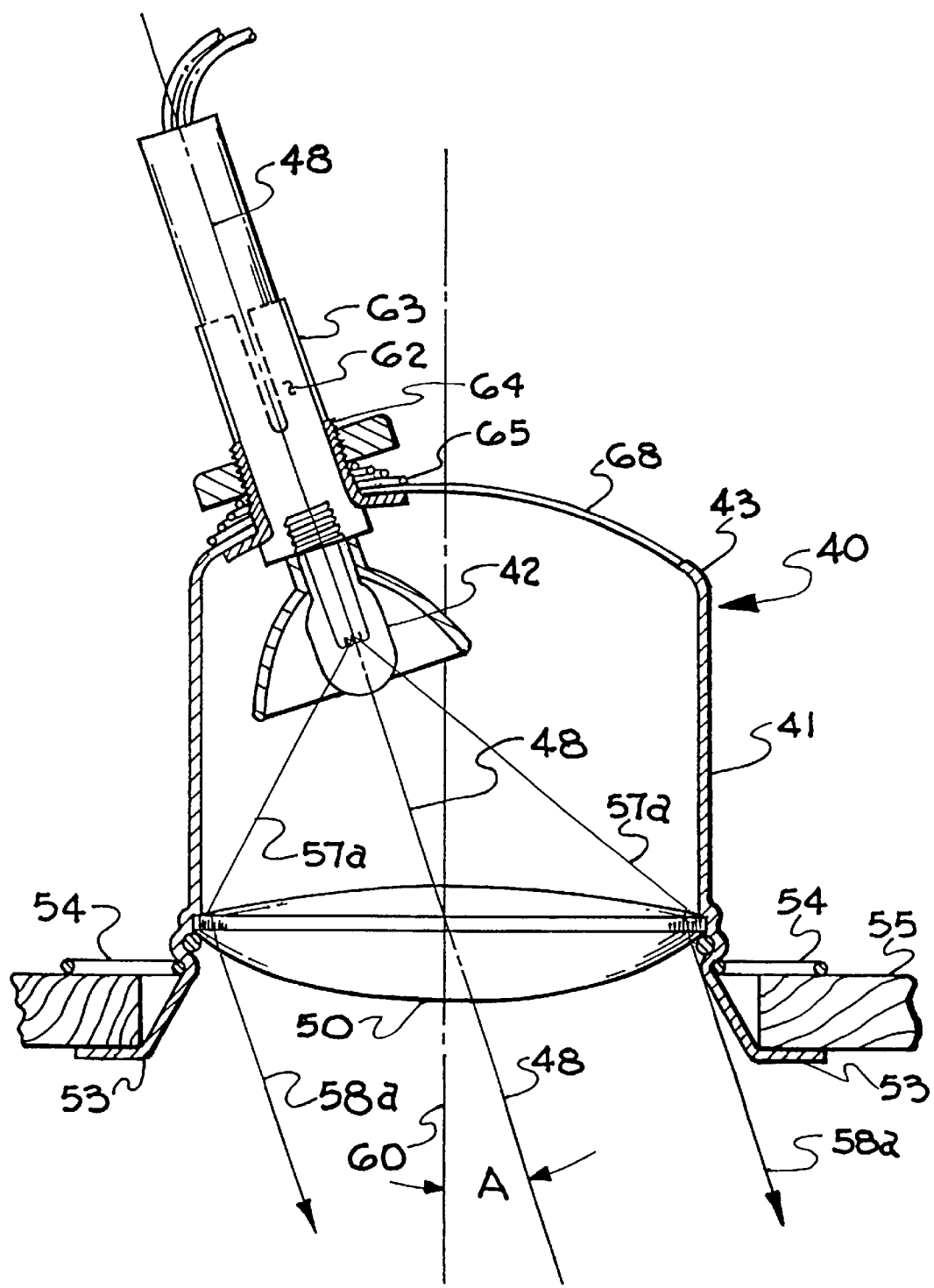
FIG. 6 is a side cross-sectional view of an aimable-beam luminaire according to the present invention, shown producing a narrow spotlight beam off the nadir axis.

In FIG. 6 a side cross-sectional view of an aimable-beam luminaire 40 according to the present invention is shown with the lamp 42 in a generally cylindrical housing 41 having a proximal end 43 and a distal end 44. Lamp 42 is positioned at the focus 45 of a lens 50 and on optical axis 48. Tube 64 distal end 65 is axial frictionally engaged through spring 65 and flange 66 within arcuate slot 68, and is shown moved transversely across proximal end 43 of housing 41 to be positioned at angle A with respect to nadir axis 60. Thus, off-axis light rays 57a from lamp 42 are generally collimated by lens 50, producing an off-axis narrow spotlight beam 58a at angle A with respect to nadir axis 60.

Figure 7:
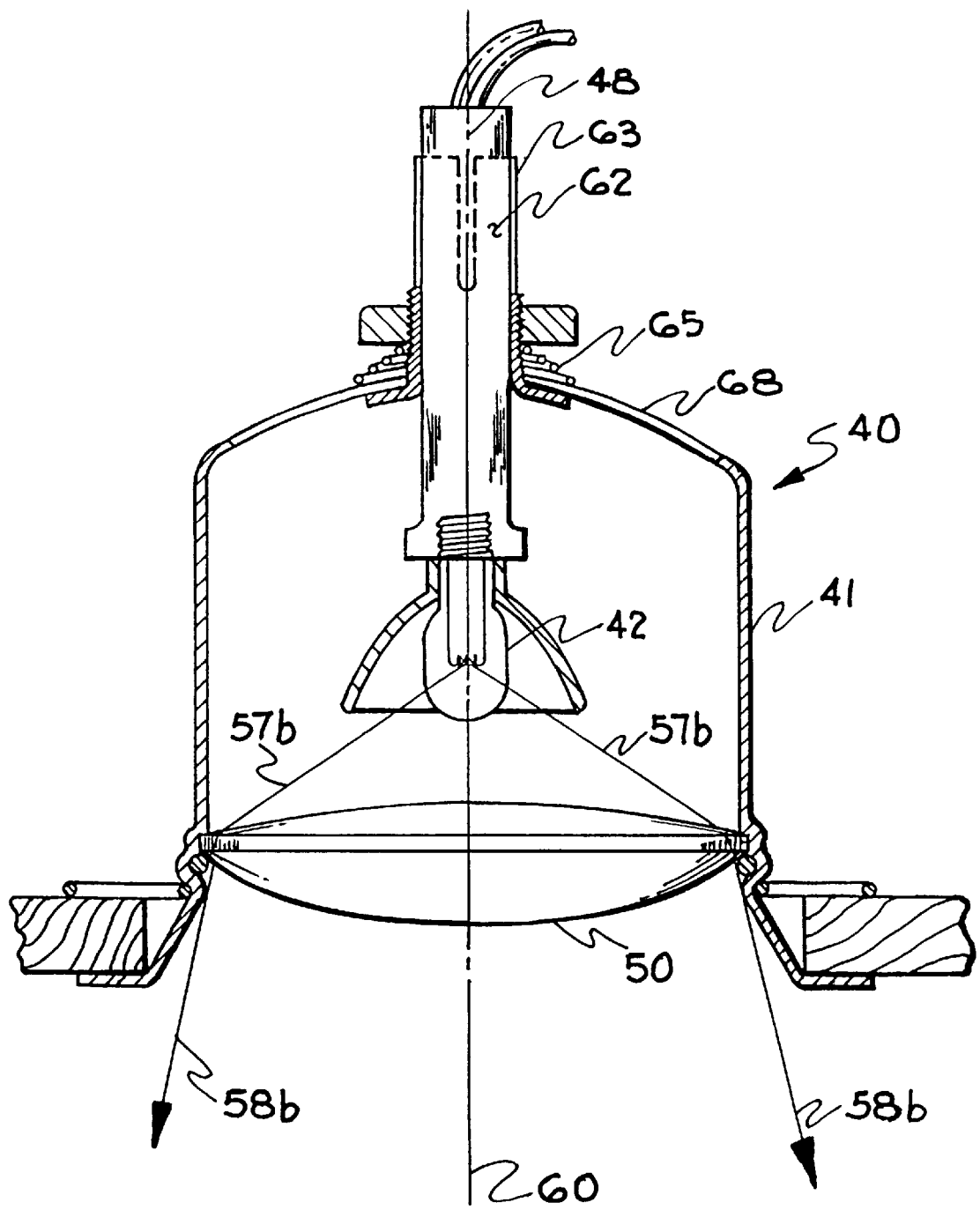
FIG. 7 is a side cross-sectional view of an aimable-beam luminaire according to the present invention, shown producing a wide floodlight beam on the nadir axis.

In FIG. 7 a side cross-sectional view of an aimable-beam luminaire 40 according to the present invention is shown with the lamp 42 positioned out of focus of lens 50, but on optical axis 48 and on nadir axis 60. Light rays 57b from lamp 42 are spread by lens 50, producing a wide floodlight beam 58b concentric about nadir axis 60.

Figure 8:
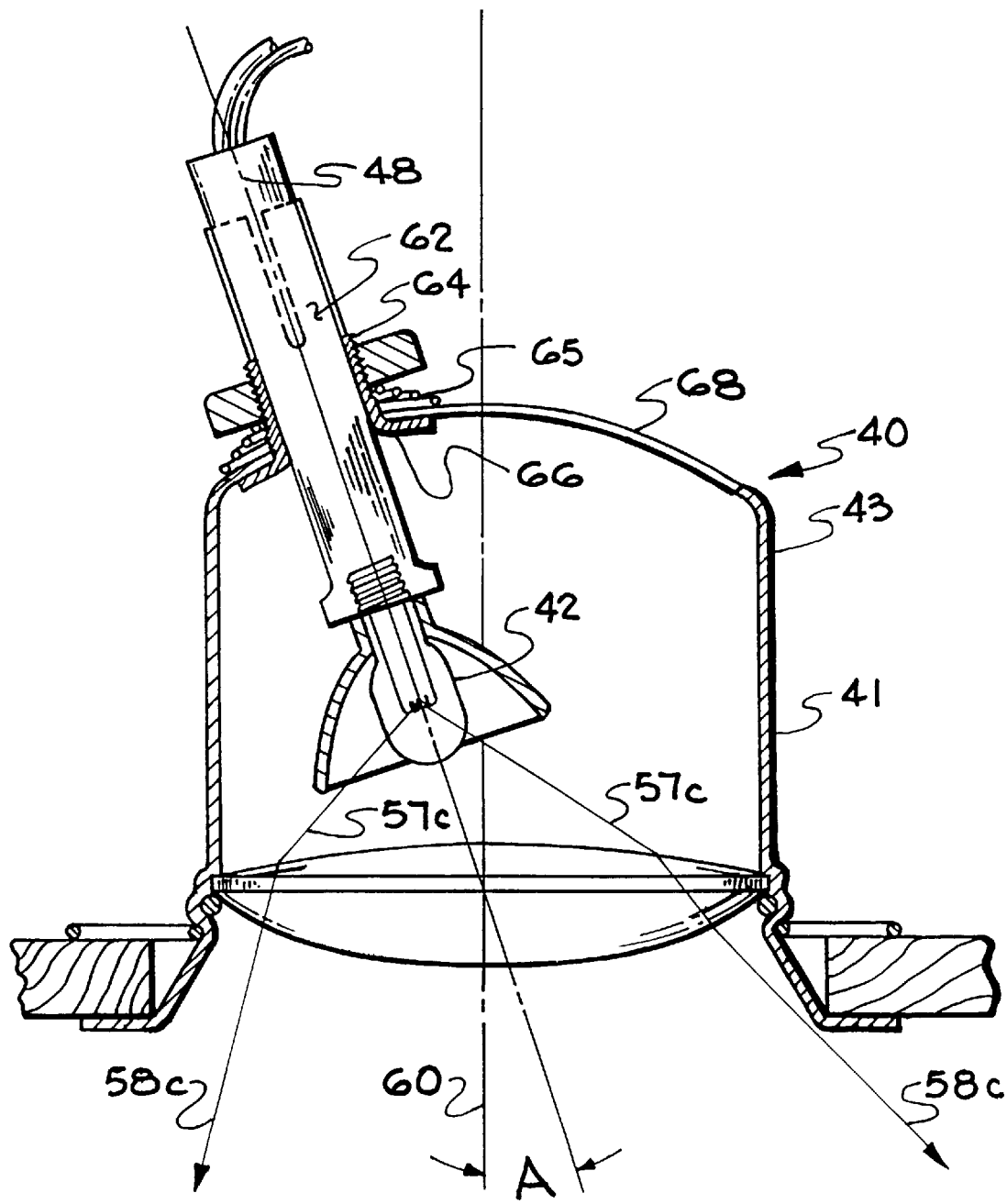
FIG. 8 is a side cross-sectional view of an aimable-beam luminaire according to the present invention, shown producing a wide floodlight beam off the nadir axis.

In FIG. 8 a side cross-sectional view of an aimable-beam luminaire 40 according to the present invention is shown with the lamp 42 in cylindrical 41. Lamp 42 is positioned out of focus of lens 50 to produce a wide floodlight beam as shown in FIG. 7. Tube 64 is frictionally engaged through spring 65 and flange 66 within arcuate slot 68 in proximal end 43 of housing 41, and is shown moved transversely across arcuate slot 68 to be positioned at angle A with respect to nadir axis 60. Thus, off-axis light rays 57a from lamp 42 are generally spread by lens 50, producing an off-axis, wide floodlight beam 58a at angle A with respect to nadir axis 60.

OPERATION

In operation, an aimable fiber-optic spotlight luminaire according to the invention has a housing and lens fixed on a central (nadir) optical axis through the lens and housing, mounting in a planar surface such as a ceiling or cabinet top. A lamp emits light from a second end within the housing, held by a lampholder within a tubular light guide retainer. The tubular retainer and is transversely adjustable in a slot across the proximal end of the housing to move the lamp off the central axis lens and housing, causing the beam formed by the lens to be aimed in elevation off the central axis. The housing, or at lease the proximal end of the housing, may be rotated in any azimuth direction, whereby an emitted beam can be aimed anywhere within the cone subtended by the rotation of the maximum off-axis angle of the light beam projected by the lens. The tubular retainer also permits axial adjustment of the end of the light guide with respect to the lens, whereby the light beam, at any azimuth or elevation location, can be zoomed between a spotlight small beam and large floodlight beam, or any desired bean angle therebetween. The lens is removable from the distal end below the ceiling plane, whereby the lamp can be replaced or axially or transversely repositioned from beneath, after which the lens may be replaced by simply re-installing a resilient retaining ring.

What is claimed is:

1. An aimable-beam luminaire (40) including:
    a generally cylindrical tubular housing (41) having a proximal end (43), a distal end (44) and an optical axis (60) therethrough;
    a lens (50) on the optical axis at the distal end of the housing and having a focus (45) within the housing;
    a lamp (42) within the housing approximately at the lens focal plane;
    a lampholder (64) for holding the lamp near the proximal end of said housing, said lampholder having means for transverse adjustment off the nadir axis whereby the lens may be positioned to project light from said lamp into a light beam at an off-axis elevation angle (A) with respect to the nadir axis of the lens and housing;
    means (53,54) for supporting and rotating the housing in a planar ceiling (55) whereby the off-axis beam projected by the lens may also be aimed in azimuth;
    means (51) for removing the lens from the distal end of the housing with the luminaire mounted in said ceiling, whereby the lamp may be replaced and the axial and transverse positions of the lamp may be positioned by reaching through the distal end of the housing from below said ceiling.

2. An aimable-beam luminaire (40) including:
    a generally cylindrical tubular housing (41) having a proximal end (43), a distal end (44) and an optical axis (60) therethrough;
    a lens (50) on the optical axis at the distal end of the housing and having a focus within the housing;
    a lamp (42) in a lampholder (64) within the housing approximately at the lens focus, said lampholder having means for transverse adjustment off the nadir axis (60) whereby the lens projects a light beam at an off-axis elevation angle with respect to the nadir axis of the lens and housing, said lampholder also having means for axial adjustment of the position of the lamp with respect to the lens;
    means (48,63) for axially or transversely adjusting the lamp position from outside the proximal end of the housing;
    means for supporting and rotating the housing in a ceiling whereby the off-axis beam projected by the lens may also be aimed in azimuth;
    means (51) for removing the lens from the distal end of the housing with the luminaire mounted in a ceiling, whereby the lamp may be replaced and the axial and transverse positions of the lamp may be positioned by reaching through the distal end of the housing from below the ceiling.

3. An aimable-beam luminaire according to claim 1 or 2 in which the lampholder frictionally retains the lamp in the axial direction.

4. An aimable-beam luminaire according to claim 1 or 2 in which the lampholder frictionally retains the lamp in the transverse direction.

5. An aimable-beam luminaire according to claim 1 or 2 in which the lampholder (48,63,64) frictionally retains the lamp in the transverse direction along a arcuate slot (68) in the housing.

6. An aimable-beam luminaire according to claim 1 or 2 in which the lampholder (48,63,64) frictionally retains the lamp in the transverse direction along an arcuate slot (68) in the housing, said arcuate slot following an arc about the optical center of the lens.

7. An aimable-beam luminaire according to claim 1 or 2 in which means for supporting and rotating the housing is an enlarged flange (53) on one side of the ceiling and a resilient member (54) on the other side of said ceiling.

\* \* \* \* \*